United States Patent
Jordan et al.

(10) Patent No.: US 6,350,119 B1
(45) Date of Patent: Feb. 26, 2002

(54) SELECTION OF ORTHODONTIC APPLIANCES

(75) Inventors: Russell A. Jordan, Rancho Cucamonga; James D. Hansen, Pasadena, both of CA (US); Yang Zhu, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/567,163

(22) Filed: May 8, 2000

Related U.S. Application Data

(62) Division of application No. 09/078,879, filed on May 14, 1998, now Pat. No. 6,089,868.

(51) Int. Cl.$^7$ ................................. A61C 3/00
(52) U.S. Cl. ........................... 433/23; 206/396
(58) Field of Search .................. 433/23, 24; 206/368, 206/369, 63.5

(56) References Cited

U.S. PATENT DOCUMENTS

| | | | |
|---|---|---|---|
| 3,861,044 | A | 1/1975 | Swinson, Jr. |
| 4,204,325 | A | 5/1980 | Kaelble |
| 4,528,627 | A | 7/1985 | Coben |

(List continued on next page.)

FOREIGN PATENT DOCUMENTS

| | | |
|---|---|---|
| DE | 38 10 455 A1 | 10/1989 |
| DE | 196 51 233 A1 | 6/1998 |
| EP | 0 502 227 A1 | 9/1992 |
| EP | 0 634 150 A2 | 1/1995 |
| EP | 0696444 | 2/1996 |
| EP | 0595231 | 4/1997 |
| IL | 114591 | 7/1995 |
| IL | 118523 | 5/1996 |
| IL | 120867 | 5/1997 |
| IL | 120892 | 5/1997 |
| IL | 121872 | 9/1997 |
| WO | WO 90/08512 | 8/1990 |
| WO | WO 96/28112 | 9/1996 |
| WO | WO 97/03622 | 2/1997 |

OTHER PUBLICATIONS

"The Orthos Approach . . . The First Comprehensive Appliance System Designed to Address Common Clinical Problems," Product literature of Ormco Company, 7 pages (undated).

(List continued on next page.)

Primary Examiner—Todd E. Manahan
(74) Attorney, Agent, or Firm—James D. Christoff

(57) ABSTRACT

A computer implemented method of orthodontic appliance selection includes providing data representative of one or more teeth of a patient and providing data representative of a set of orthodontic appliances. Each orthodontic appliance of the set of orthodontic appliances has an appliance parameter that varies from the other orthodontic appliances of the set. At least one geometrical parameter of the one or more teeth of the patient is determined using the data representative thereof. The geometrical parameter is compared to the data representative of the set of orthodontic appliances and one orthodontic appliance of the set is selected based on the comparison. The set of orthodontic appliances may be a set of orthodontic bands with each band of the set having a different size. Further, such bands may be precoated with an adhesive material. A computer readable medium tangibly embodying a program executable for use in selection of orthodontic appliances, a system for use in orthodontia using such selection, and a method of fitting an orthodontic band to a patient are also provided. Further, an article including a container and a set of precoated bands received therein is provided.

3 Claims, 10 Drawing Sheets

U.S. PATENT DOCUMENTS

| | | |
|---|---|---|
| 4,611,288 A | 9/1986 | Duret et al. |
| 4,668,192 A | 5/1987 | Lavin |
| 4,742,464 A | 5/1988 | Duret et al. |
| 4,761,135 A * | 8/1988 | Steinkohl ..................... 433/23 |
| 4,837,732 A | 6/1989 | Brandestini et al. |
| 4,919,615 A | 4/1990 | Croll |
| 4,964,770 A | 10/1990 | Steinbichler et al. |
| 5,011,405 A | 4/1991 | Lemchen |
| 5,027,281 A | 6/1991 | Rekow et al. |
| 5,078,599 A | 1/1992 | Eenboom et al. |
| 5,131,844 A | 7/1992 | Marinaccio et al. |
| 5,139,419 A | 8/1992 | Andreiko et al. |
| 5,212,871 A | 5/1993 | Luccarelli |
| 5,237,998 A | 8/1993 | Duret et al. |
| 5,266,030 A | 11/1993 | Van Der Zel |
| 5,278,756 A | 1/1994 | Lemchen et al. |
| 5,322,436 A | 6/1994 | Horng et al. |
| 5,338,198 A | 8/1994 | Wu et al. |
| 5,342,194 A | 8/1994 | Feldman |
| 5,354,199 A | 10/1994 | Jacobs et al. |
| 5,368,478 A | 11/1994 | Andreiko et al. |
| 5,372,502 A | 12/1994 | Massen et al. |
| 5,395,238 A | 3/1995 | Andreiko et al. |
| 5,417,572 A | 5/1995 | Kawai et al. |
| 5,441,409 A * | 8/1995 | Tuneberg ..................... 433/23 |
| 5,454,717 A | 10/1995 | Andreiko et al. |
| RE35,169 E | 3/1996 | Lemchen et al. |
| 5,518,397 A | 5/1996 | Andreiko et al. |
| 5,533,895 A | 7/1996 | Andreiko et al. |
| 5,538,129 A | 7/1996 | Chester et al. |
| 5,575,645 A | 11/1996 | Jacobs et al. |
| 5,605,459 A | 2/1997 | Kuroda et al. |
| 5,674,069 A | 10/1997 | Osorio |
| 5,683,243 A | 11/1997 | Andreiko et al. |
| 5,759,028 A * | 6/1998 | Bozman ..................... 296/369 |
| 5,851,115 A | 12/1998 | Carlsson et al. |
| 5,879,158 A | 3/1999 | Doyle et al. |
| 5,882,192 A | 3/1999 | Bergersen |

OTHER PUBLICATIONS

"Biomechanics in Orthodontics," Product literature of Giorgio Fiorelli—Birte Melsen, 2 pages (undated).

T. Kuroda et al., "Three–dimensional dental cast analyzing system using laser scanning," *J. Am. Ortho. Dent. Orthop.*, 110, 365–369 (Oct. 1996).

D. Laurendeau et al., "A Computer–Vision Technique for the Acquisition and Processing of 3-D Profiles of Dental Imprints: An Application in Orthodontics," *IEEE Transactions on Medical Imaging, 10,* 453–461 (Sep. 1991).

* cited by examiner

SELECTION OF ORTHODONTIC APPLIANCES

This is a division of application Ser. No. 09/078,879, filed May 14, 1998 now U.S. Pat. No. 6,089,868 which is incorporated herein by reference.

FIELD OF THE INVENTION

The present invention relates to orthodontia. More particularly, the present invention relates to the selection of orthodontic appliances, e.g., orthodontic bands.

DESCRIPTION OF THE RELATED ART

Orthodontic treatment involves movement of the teeth to desired positions. During treatment, small slotted bodies (known as brackets) are typically bonded to anterior teeth, and an arch wire held in the slots functions as a track to guide movement of the teeth. Teeth are commonly moved by bends or twists placed in the arch wire, or by elastic members connected between the brackets of certain teeth.

Ends of the arch wires are normally anchored in devices known as buccal tubes that are mounted on molar teeth. Occasionally, buccal tubes are bonded directly to an exterior surface of the molar teeth using a small amount of adhesive in a manner similar to the method of bonding brackets directly to anterior teeth. However, buccal tubes are often subjected to relatively large forces from occluding teeth, as well as forces exerted by the arch wire. As a result, the buccal tubes may spontaneously debond from the tooth. Rebonding of the buccal tube can be achieved, but is a nuisance both to the orthodontist and the patient.

As a consequence, buccal tubes are commonly welded to metallic orthodontic bands that are placed around the molar teeth to provide a stable base for mounting the buccal tubes. Orthodontic bands are made in a variety of shapes and sizes so that a band with the proper contour and circumferential dimensions can be selected in each instance to tightly fit onto the molar tooth. Bands are also available for use with anterior, cuspid, and bicuspid teeth in instances where a relatively strong connection to such teeth is desired.

Band selection is often made by the orthodontist by first visually estimating the size of the chosen tooth and then selecting a few bands of different sizes that appear to be close in size to the tooth. Generally, the method of fitting such bands is for the orthodontist to place a band over the tooth and "feel" how it fits. Different size bands are trial fitted until an acceptable fit, or best-fit, is found.

During the fitting procedure, the bands selected by the orthodontist are placed on a set-up tray that is located by the patient. Once the best-fit band is found, the remaining bands are sterilized to reduce the risk of cross-contamination before being returned to a storage container, i.e., reinventoried.

Typically, orthodontic bands need to fit around the tooth geometry in a fairly precise manner to allow for good performance. After the proper orthodontic band is selected, the band is subjected to a burnishing process wherein a rotating tool is used to form the band to fit the contours of the tooth. Orthodontic bands have a fundamental geometry that stays constant throughout the size range. Generally, the different sizes of the orthodontic bands are made by scaling a fundamental geometry up or down.

The manual method of fitting an orthodontic band to the tooth, as described above, is a very time consuming process. Further, this manual process requires that trial bands be sterilized and reinventoried after the best fit band is found.

SUMMARY OF INVENTION

The present invention is directed toward orthodontic appliance selection that is performed in an automatic manner instead of a manual fitting process as described in the Background of the Invention section. In one embodiment of the invention, a computer implemented method compares tooth geometry to known band geometry such that a properly sized band can be selected without manual fitting techniques.

A computer implemented method of orthodontic appliance selection according to the present invention includes providing data representative of one or more teeth of a patient and providing data representative of a set of orthodontic appliances. Each orthodontic appliance of the set of orthodontic appliances has an appliance parameter that varies from the other orthodontic appliances of the set. At least one geometrical parameter of the one or more teeth of the patient is determined using the data representative thereof. The at least one geometrical parameter is compared to the data representative of the set of orthodontic appliances and one orthodontic appliance of the set of orthodontic appliances is selected based on the comparison.

In one embodiment of the method, the set of orthodontic appliances includes a set of orthodontic bands with each band of the set having a different size. Such bands may be precoated with an adhesive material.

In one embodiment of the band selection method, the determination of the geometrical parameter of the one or more teeth of the patient includes determining a geometrical parameter associated with a portion of a tooth of the patient that lies orthogonal to a center axis of the tooth, e.g., a perimeter length of a cross-section of the tooth of the patient, an area of a cross-section of the tooth, a volume of a section of the tooth, a width of a cross-section of the tooth, etc. In other embodiments of the method, the center axis may be determined based on a best fit cylinder for data representative of the tooth or based on a best fit occlusal plane for the data representative of the tooth.

A method for use in orthodontia is also described. The method includes generating data representative of at least one geometrical parameter of a tooth of a patient and providing data representative of a set of orthodontic bands. Each orthodontic band of the set has an associated band parameter different from the other orthodontic bands of the set. The at least one geometrical parameter is compared to the data representative of the set of orthodontic bands and one of the set of orthodontic bands is selected based on the comparison. The selected band is applied to the tooth. In different embodiments of the method, the set of orthodontic bands may or may not be precoated with an adhesive material.

A computer readable medium tangibly embodying a program executable for use in selection of orthodontic appliances includes a program portion for recognizing data representative of one or more teeth of a patient and for recognizing data representative of a set of orthodontic appliances. Each orthodontic appliance of the set of orthodontic appliances has an appliance parameter that varies from the other orthodontic appliances of the set. The program further determines at least one geometrical parameter of the one or more teeth of the patient using the data representative thereof. Further, a comparison of the at least one geometrical parameter is made to the data representative of the set of orthodontic appliances and one orthodontic appliance of the set of orthodontic appliances is selected based on the comparison.

A system for use in orthodontia according to the present invention includes memory storing data representative of at least one geometrical parameter of a tooth of a patient and memory storing data representative of a set of orthodontic bands. Each orthodontic band of the set has an associated band parameter different from the other orthodontic bands of the set. The system further compares the at least one geometrical parameter to the data representative of the set of orthodontic bands and selects one of the set of orthodontic bands based on the comparison.

A method of fitting an orthodontic band to a tooth of a patient according to the present invention is also described. The method includes providing a set of orthodontic bands with at least a portion of each orthodontic band coated with an adhesive material. The method further includes selecting one orthodontic band of the set of orthodontic bands based on a geometrical parameter of the tooth of the patient. Thereafter, the selected band is applied to the tooth of the patient.

An article according to the present invention includes a container and a set of orthodontic bands received in the container. Each of the set of orthodontic bands has substantially a same fundamental geometrical configuration and each of the orthodontic bands is of a different size relative to the other orthodontic bands. Further, each orthodontic band has a precoat adhesive material applied to at least a portion thereof.

DETAILED DESCRIPTION OF THE EMBODIMENTS

The present invention shall be described generally with reference to FIGS. 1–7. Thereafter, the present invention shall be described in further detail with reference to FIGS. 8A–8E and 9A–9E.

As used herein, digital data refers to digital data captured directly from a patient's anatomy in a digital form (e.g., teeth, gums, etc.) by any method (e.g., stereographs, digitization probes, optical scanning and detection devices, etc.), or captured indirectly from a patient by removing information regarding the patient's anatomy in a non-digital form (e.g., dental impressions, study models, x-rays, etc.) and then digitizing such information by any method (e.g., slicing the impressions and digitizing boundaries, using an optical scanning detection device, etc.). Such digital data may be actual measured digital data or calculated digital data such as three-dimensional surface data generated using such actual measured digital data.

Figure 1:
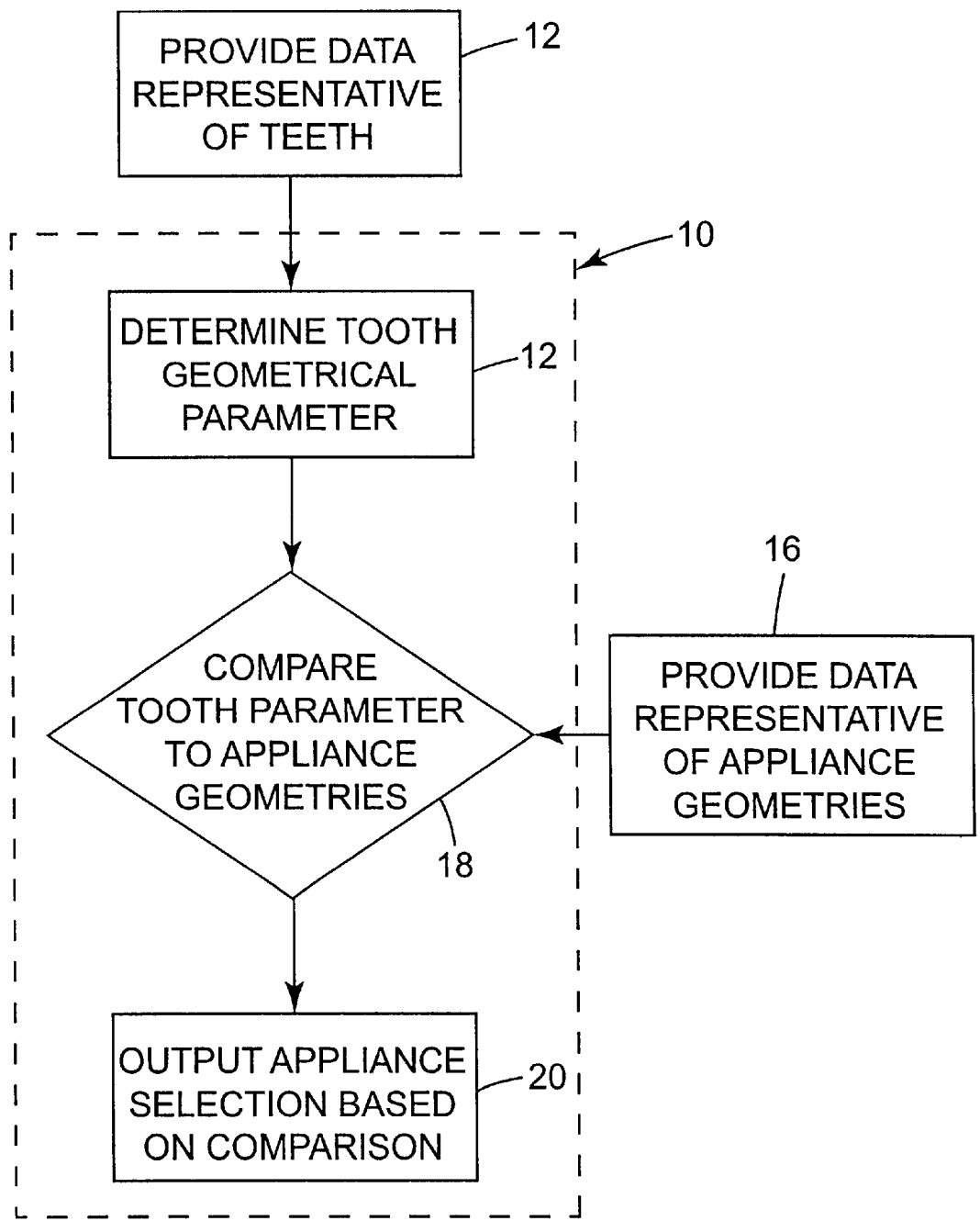
FIG. 1 is a flow diagram for a method of orthodontic appliance selection in accordance with the present invention.
Figure 2:
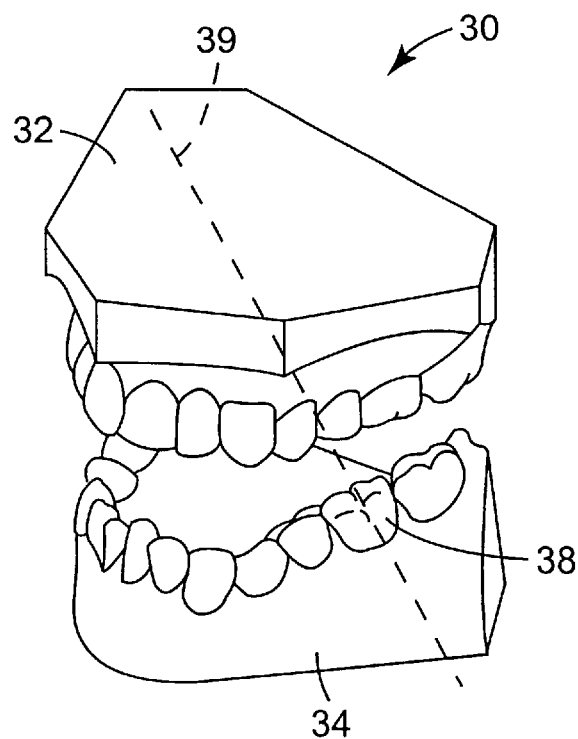
FIG. 2 is a generalized representation of an image of a patient's upper and lower arches for which an orthodontic appliance is needed.
Figure 3:
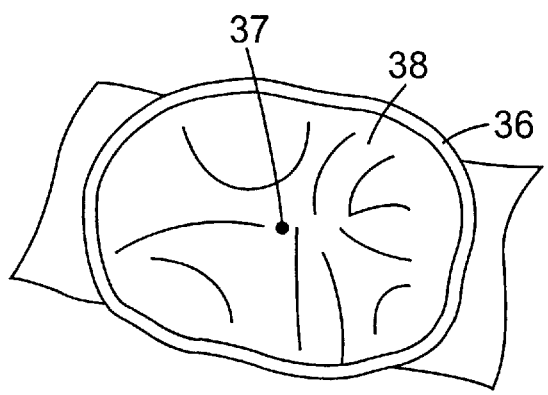
FIG. 3 is a more detailed diagram of a tooth of FIG. 2 with an orthodontic band applied thereto.

FIG. 1 shows a flow diagram of an orthodontic appliance selection method 10 according to the present invention. The orthodontic appliance selection method 10 uses digital data representative of one or more teeth of a patient (Block 12) and data representative of one or more geometrical parameters of a set of orthodontic appliances (Block 16) to select a suitable orthodontic appliance for use on one or more teeth of a patient. The patient's teeth 30 are represented by the lower arch 34 and upper arch 32 images generally shown in FIG. 2.

The selection method 10 includes determining one or more geometrical parameters of one or more teeth (Block 14) using the input digital data representative of the one or more teeth (Block 12). The one or more determined geometrical parameters are then compared (Block 18) to the input data representative of corresponding geometrical parameters of a set of orthodontic appliances (Block 16), i.e., geometrical parameters corresponding to the one or more geometrical parameters of one or more teeth. An output orthodontic appliance selection is then generated (Block 20) based on the comparison performed (Block 18).

For example, and for which illustrative embodiments are provided in further detail below, the data provided in Block 12 may be digital data representative of a single tooth, and the data provided in Block 16 may be data representative of one or more geometrical parameters of a set of orthodontic bands, e.g., precoated orthodontic bands. The selection method 10 is then used to determine one or more geometrical parameters of the tooth, as shown by Block 14. The one or more geometrical parameters of the tooth are then compared with the data representative of geometrical parameters of a set of orthodontic bands as shown by the comparison Block 18. Thereafter, an output representing an appropriately sized orthodontic band is generated (Block 20) based on the comparison (Block 18). In accordance with these illustrative examples, an orthodontic band 36 (FIG. 3) is selected for use on tooth 38 of lower arch 34. The orthodontic band 36 has a center axis 37 extending therethrough that is aligned with a long axis 39 of tooth 38 when the orthodontic band is applied to tooth 38, e.g., a molar.

Generally, further with reference to the selection method 10, the data representative of the teeth (Block 12) includes digital data representative of the structure of one, more than one, or all of the teeth of a patient and may also include the relevant gingiva. There are a variety of methods available for providing such information. The present invention is not limited to any particular method but only as described in the accompanying claims.

For example, tools which can be used to provide digital data representative of one or more teeth or entire upper and lower dental arches may include dental impressions, laser scans, stylist scans, and/or stereophotographs. The digital data concerning the one or more teeth may be captured directly from the patient in a digital form, e.g., stereographs, or the information may be captured indirectly from the patient by removing the information from the patient in a non-digital form (e.g., dental impressions and study models) and later digitizing the information (e.g., slicing the dental impressions and digitizing the boundaries). Some of the varied processes for providing digitized data of one or more teeth or entire dental arches include, but are clearly not limited to, laser scanning, photogrammetry, and those processes described in U.S. Pat. No. 5,078,599; U.S. Pat. No. 5,131,844; U.S. Pat. No. 5,338,198; U.S. Pat. No. 4,611,288; U.S. Pat. No. 5,372,502; the article, entitled "Three-Dimensional dental cast analyzing system with laser scanning," by T. Kuroda, et al., Am.J.Ortho.Dent.Othrop., Vol. 110 [4], October 1996, pp. 365–69; and Israeli Patent Application Serial Nos. 118,523 (filed May 31, 1996) and 114,691 (filed Jul. 20, 1995) and both entitled "Method and System for Acquiring Three-Dimensional Teeth Image."

The particular illustrative method described in the Israeli Patent Applications acquires a dental image by removing layers of an impression on a dental image tray, or by removing layers of a model made from such an impression. As each layer is removed, a two-dimensional image is obtained by a video camera of the remaining flat surface. Data representative of the boundaries of the two-dimensional images representing the surfaces of the teeth and adjacent gingiva are stored by a computing system. Once a sufficient number of layers have been removed, the computing system combines the two-dimensional images of the captured layers into a three-dimensional created image that represents at least a portion of the patient's teeth and gingiva, e.g., one or more teeth.

Surfaces, or calculated elements, may be generated between actual measured data points representative of the one or more teeth. As such, the digital data may include calculated data representative of surfaces of the one or more teeth, as opposed to measured digital data from which the calculated digital data is generated. Such calculated digital data for display of surfaces can be generated in numerous ways from the measured digital data, as would be known to one skilled in the art. The resulting calculated data may be representative of various elements used for display of such surfaces, e.g., various calculated points, meshes, polygons, etc.

Generally, the data representative of geometrical parameters of orthodontic appliances (Block 16) includes data representative of one or more geometrical parameters which can be compared to geometrical parameters of one or more teeth as determined in accordance with Block 14. In a preferred embodiment of the present invention, the data representative of the geometrical parameters of an orthodontic appliance includes one or more geometrical parameters of a set of orthodontic bands.

Such bands shall be generally described with reference to the illustrative bands of FIGS. 5–7. One skilled in the art will recognize that the configuration of such bands may differ depending upon the manufacturer and the particular teeth upon which the bands are to be used (e.g., first molar, second molar, etc.).

Figure 5:
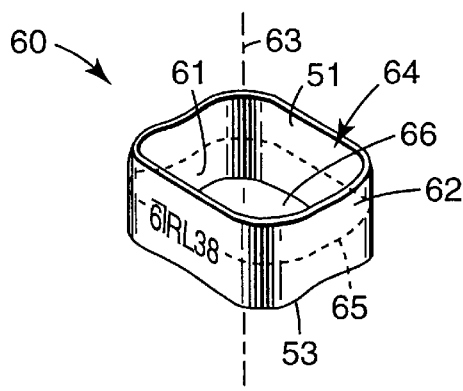
FIG. 5 is an illustrative perspective view of an orthodontic band.

The orthodontic band 60, as shown in FIG. 5, is made of a metallic material, preferably stainless steel type 305. The band 60 has an axis 63 extending therethrough. The band 60 has a height, contour, and inner circumference along inner surface 61 that closely matches the expected shape of particular teeth without interference with the gingiva. The band 60 includes a body 62 having inner surface 61. The body 62 extends from a first end 53 defining opening 66 to a second end 51 defining opening 64. Both the first and second ends 51, 53 have an inward extending contour shape, i.e., the ends of the bands lie closer to the axis 63 than the portion of the body at a center line 65 of the band. The remainder of the body 62 is substantially vertical. The center line 65, lying in a plane orthogonal to axis 63 is located within the vertical portion of the body 62 between the first and second ends 51, 53 of the orthodontic band 60. At such a center line 65, the circumferential or perimeter length along the inner surface 61 of the orthodontic band 60 is a geometrical parameter of the band which can be compared in length to a maximum perimeter or circumferential length about the tooth in a plane orthogonal to the center axis, i.e., long axis, of the tooth. For example, such a comparison can be made to select an appropriate band for the tooth.

The orthodontic band 60 is typically applied to the tooth with a "snap fit." The band after application to the tooth is typically subjected to a burnishing process wherein a tool is used to form the band 60 to the contours of the tooth. As applied, the axis 63 of the band 60 is substantially aligned with the center axis, i.e., the long axis, of the tooth upon which it is applied.

Figure 6:
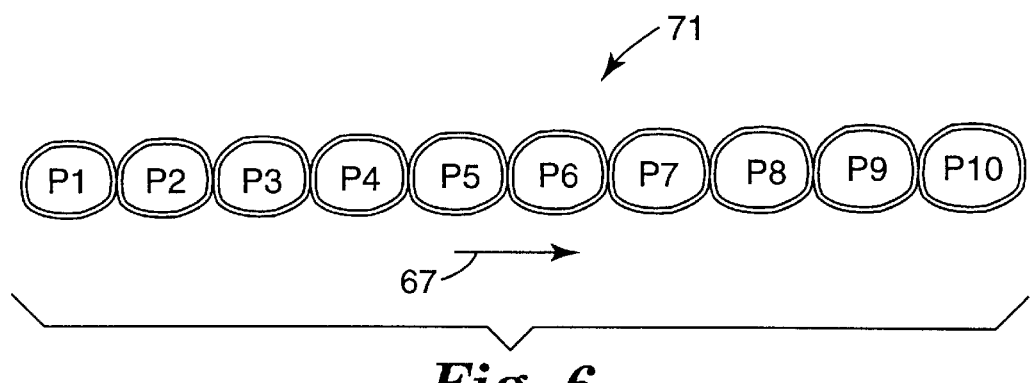
FIG. 6 is a diagram illustrating size differentials between a set of orthodontic bands.

An illustrative set of orthodontic bands 71 is shown in FIG. 6. Generally, each band of the set of orthodontic bands 71 have a fundamental geometry scaled up or down in size. For example, the perimeter length along the inner surface 61 of each band increases as the fundamental geometry of the set of bands is scaled up. As shown in FIG. 6, the perimeter length or circumferential length along the inner surface 61 increases, as shown by arrow 67, from band P1 to band P10. Each of the bands P1–P10 includes a different inner surface perimeter or circumferential length at a centerline thereof.

Figure 7A:
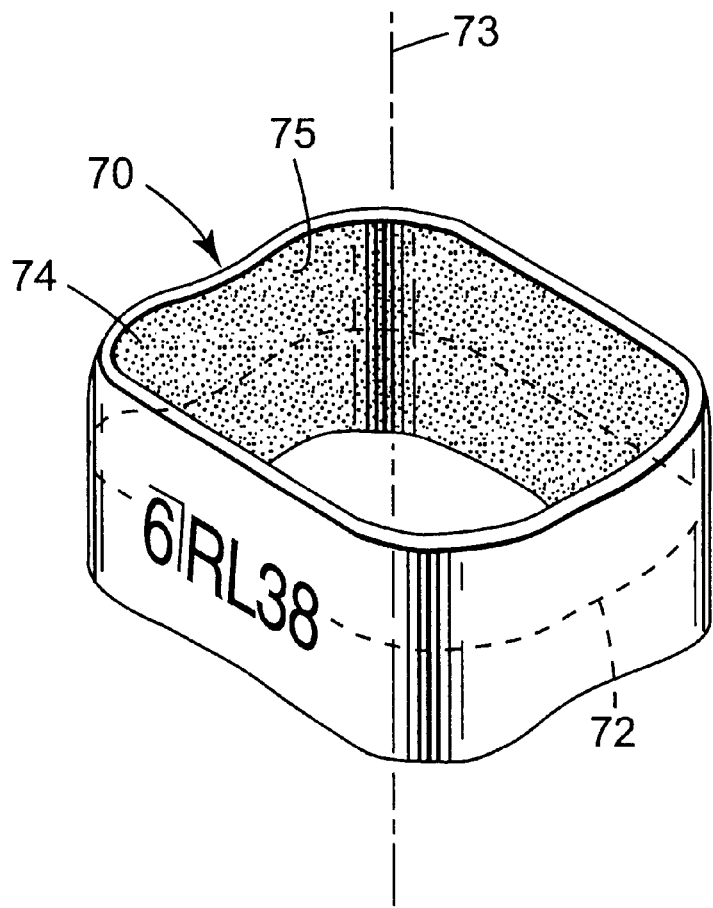
FIG. 7A is an illustrative perspective view of a precoated orthodontic band.
Figure 7B:
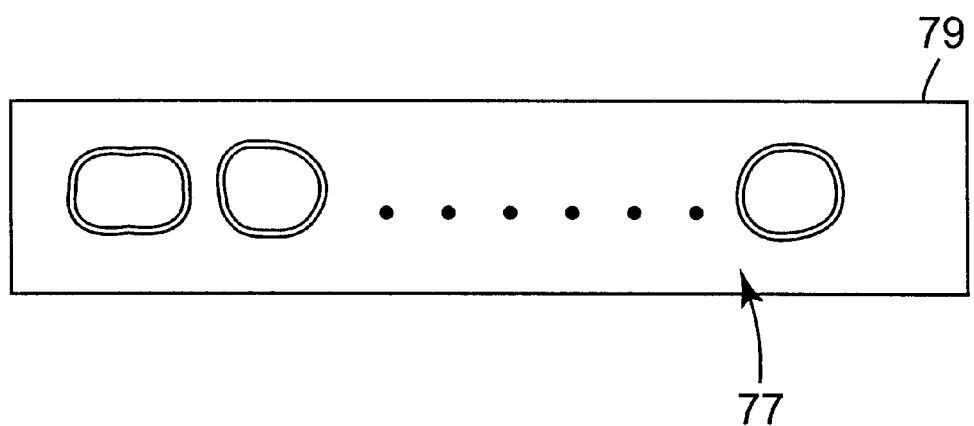
FIG. 7B is an generalized diagram of a packaged set of precoated orthodontic bands.

Further, as shown in FIG. 7B, a set of orthodontic bands 77, including bands such as precoated orthodontic band 70 shown in FIG. 7A, may be used in accordance with the present invention. Selection of orthodontic bands according to the present invention allows the orthodontic band to be precoated because the proper band is selected without the need to fit a multiple number of bands on the patient's tooth to find the best fit band. As such, the efficiency and band bonding performance is improved. In other words, a package 79 containing a set of orthodontic bands 79 having a pre-applied coating of adhesive can be provided to a user of the appliance selection method according to the present invention.

The precoated orthodontic band 70 includes axis 73 extending therethrough, along with a center line 72 representing a maximum perimeter length along inner surface 75 of the orthodontic band 70. The center line 72 lies in a plane orthogonal to axis 73. Further, the precoated orthodontic band 70 includes a band cement or adhesive coating 74 along inner surface 75 of the orthodontic band 70.

The precoat adhesive 74 may be any adhesive or coating suitable for bonding the band to the tooth. For example, such adhesive coatings or band cement may include a light curable adhesive, e.g., Transbond XT available from 3M Unitek Corp. (Monrovia, Calif.) or an adhesive described in U.S. Pat. No. 5,575,645 entitled "Adhesive For Packaged Orthodontic Appliance"; a chemical cure adhesive such as an adhesive sold under the trade designation BOND-EZE or CONCISE available from 3M Unitek Corp.; or other adhesives such as those sold under the trade designation UNITE and available from 3M Unitek Corp. or those available from Reliance Orthodontic Products (Itasca, Ill.) and Dentsply (York, Pa.).

The precoat adhesive is generally applied to at least a portion of the inside of a band in the factory. For example, as shown in FIG. 7A, the adhesive 74 can be uniformly spread across the inner surface 75 of the band. However, FIGS. 7A and 7B are generally representative of an adhesive or coating applied to any portion of the band which can be used to achieve the desired bonding characteristics. For example, the adhesive can be dispensed as a bead of material on the gingival edge of the band.

Depending upon the type of product precoated with the adhesive, different amounts of adhesive may be used. For example, for standard bands (as opposed to patient specific bands), a suitable amount of excess adhesive may be coated onto the inside surface of the band. On the other hand, for patient specific bands, the amount and distribution of adhesive can be optimized by calculating the volume misfit between the inside of the band and the tooth with application of the optimized amount of adhesive.

The precoated bands, e.g., standard or patient specific bands, can be packaged in any type of suitable container 79 as generally represented in FIG. 7B. For example, the package may include a plastic container that is a substantial barrier to light when light curable adhesives are used, such as described in U.S. Pat. No. 5,575,645. Further, such packaging may include any container that prevents curing, contamination and degradation of the adhesive, e.g., a container made of plastic, glass, metal, etc. One example of a package that could be used for the precoated bands is described in U.S. Pat. No. 5,538,129. Further, release liners can be used but would generally not be necessary because the adhesive is preferably confined to the inner surface of the band.

The use of precoated bands provide various benefits. For example, with use of a precoated band, an entire step at the clinic site is eliminated. Further, the coating is performed in a controlled environment as opposed to the clinic site. This reduces the possibility of contamination and subsequent bond failure. As previously mentioned, bands have not been precoated as such precoated bands were not practical due to the need to perform trial fitting of the bands to the patient's tooth to determine proper band size.

Figure 4:
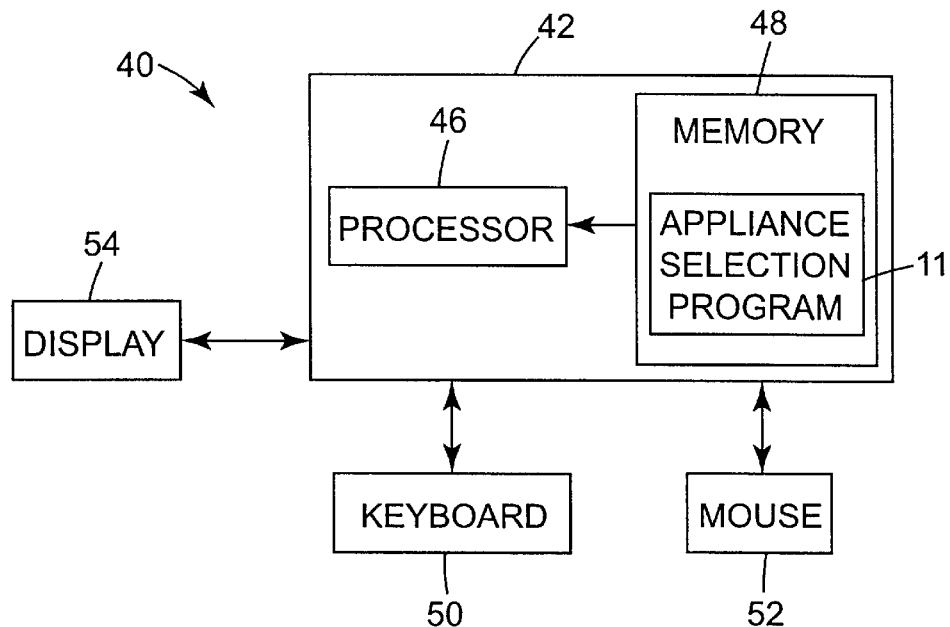
FIG. 4 is an orthodontic appliance selection system including an orthodontic appliance selection program in accordance with the present invention.

As shown in FIG. 4, a selection program 11 for performing the selection method 10 (including Blocks 14, 18, and 20 of FIG. 1) is resident in memory 48 of a computing unit 42 of an orthodontic appliance selection system 40. The computing unit 42 further includes processor 46. Further, the data representative of one or more teeth (Block 12) and the data representative of geometrical parameters of orthodontic appliances (Block 16) may also be resident in memory 48 for use by program 11 or provided as inputs to computing unit 42.

It will be readily apparent to one skilled in the art that the present invention may be adapted to be operable using any processor based system, e.g., a personal computer, and, further, that the present invention is in no manner limited to any particular processing system. The amount of memory of the system should be sufficient to allow for operation of the program 11 and storage of data, such as teeth data and geometrical parameter data, for use by program 11. It is readily apparent that such memory may be provided by peripheral memory devices. The system 40 may include any number of other peripheral devices as desired for operation of the system 40, such as, for example, the following respective devices: display 54, keyboard 50, and mouse 52. However, one skilled in the art will recognize that the system is in no manner limited to use of such devices, nor that such devices are necessarily required for operation of the system 40.

For example, the computing system 40 may be a Netpower Symetra-II with a True-TX graphics card. However, any suitable computing system may be used. Various programs and languages may be used to accomplish the functions as described herein, as would be readily apparent to one skilled in the art. For example, such functionality may be provided using $C^{++}$ language, Open GL, etc. Further, available software packages may be used for providing various functions, such as display of images, manipulation of images, etc. For example, Open Inventor available from Silicon Graphics may be used to display images and Digital Diagnostic Protocol may be used to communicate information.

Illustrative embodiments of orthodontic appliance selection methods 10, regarding selection of an orthodontic band from a set of orthodontic bands such as those shown in FIGS. 5–7, are shown and shall be described with reference to FIGS. 8A–8E and 9A–9E.

One illustrative embodiment of an orthodontic band selection method 80 according to the present invention is shown and described with reference to FIGS. 8A–8E. The orthodontic band selection method 80 includes the determination of a geometrical parameter of a tooth (dashed line Block 82), e.g., such as determination of a parameter of tooth 134 shown in FIG. 8B, from digital data representative of the tooth 134 (Block 84). The geometrical parameter determination process (Block 82) of the orthodontic band selection method 80 includes determining, e.g., via calculations, the long axis of a cylinder which best fits the tooth 134 (Block 90) from the tooth data representative of the tooth (Block 84). Using the long axis determined for the best fit cylinder, the process proceeds in a stepwise manner along the long axis. A geometrical parameter associated with a cross section of the tooth at steps along the axis is determined (Block 92). A maximum value for the geometrical parameter is then preferably determined (Block 94) from those values for the geometrical parameter determined at the steps along the axis. The maximum tooth parameter value is then used for comparison (Block 88) to data representative of band geometrical parameters (Block 86). A band selection is then output (Block 89) based on the comparison (Block 88). A resultant orthodontic band is then selected by the user of the system and applied to the tooth (Block 87), e.g., positioned on the tooth, burnished, etc. The geometrical parameter data for the bands may be stored in any form capable of being compared to the determined geometrical parameter of the tooth, e.g., look-up table, any programmable memory, database, etc.

Figure 8A:
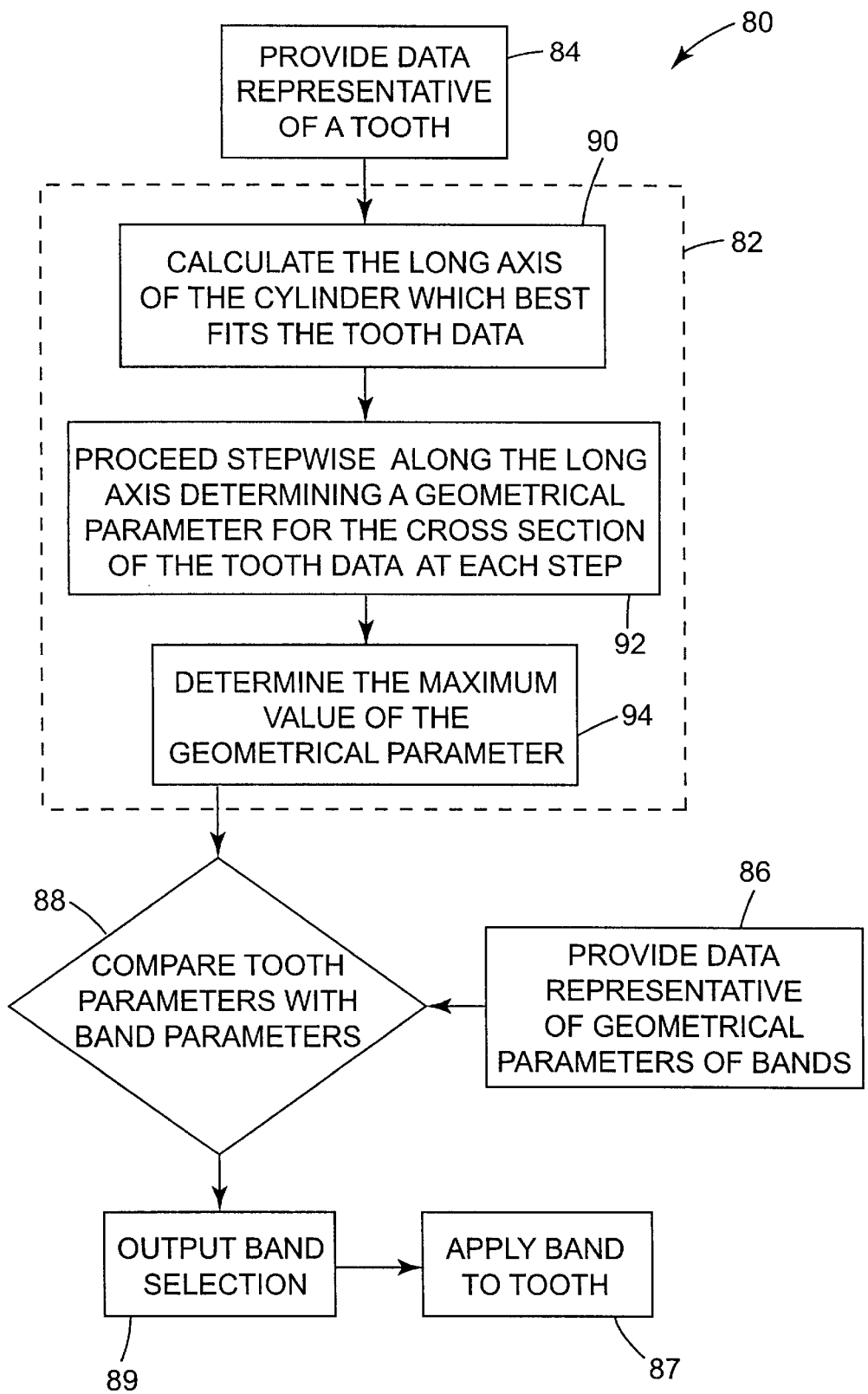
FIG. 8A is a flow diagram illustrating one embodiment of a method for orthodontic appliance selection according to the present invention.
Figure 8B:
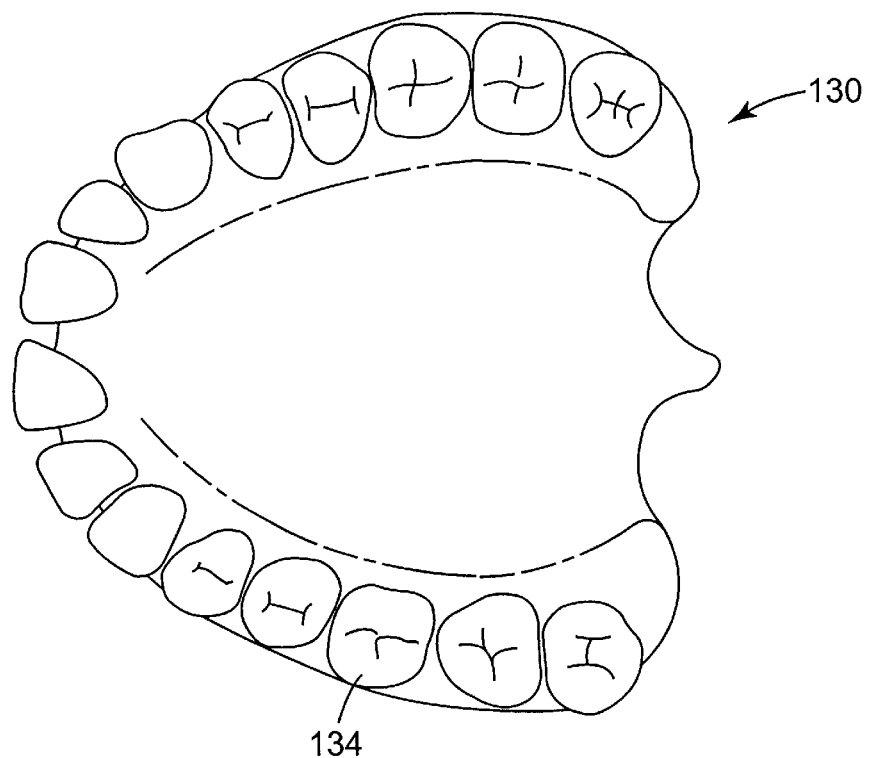
FIG. 8B is a top view of a lower arch including a tooth for which a band is to be selected in accordance with the process shown in FIG. 8A.
Figure 8C:
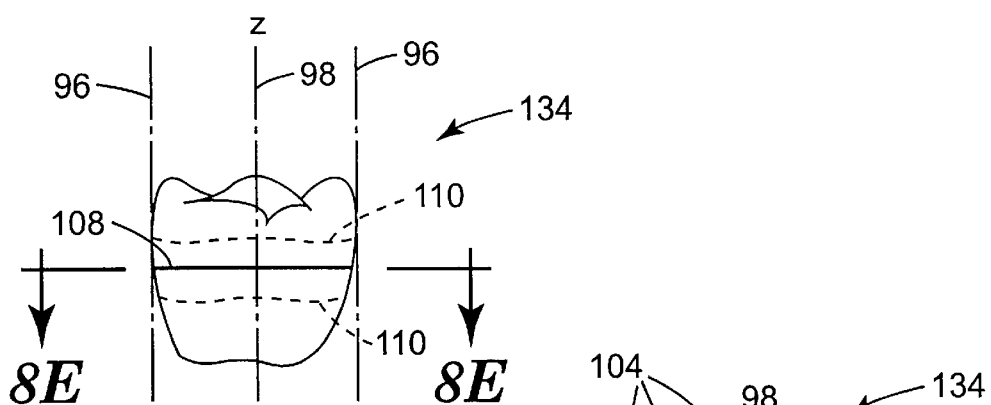
FIG. 8C is a side view of the tooth of the lower arch shown in FIG. 8B for which a band is to be selected according to the present invention.
Figure 8E:
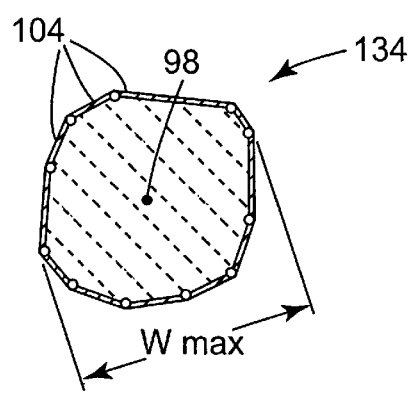
FIG. 8E is a cross-section view of the tooth of FIG. 8C taken at line 8E—8E thereof.

One skilled in the art will recognize that the geometrical parameter determined by geometrical parameter determination process 82 using the digital data representative of tooth 134 (Block 84), and the geometrical parameter determination process itself, may take one of many forms. For example, the geometrical parameter determined may be a perimeter length at a cross-section of tooth 134 at line 108 orthogonal to the long axis 98 shown in FIGS. 8C and 8E, the geometrical parameter may be the cross-section area of the slice as represented by the lined area shown in FIG. 8E, the geometrical parameter may be an integrated volume of a slice of the tooth (as represented by dashed lines 110 of FIG. 8C), the geometrical parameter may be the maximum width (Wmax) of a cross-section of the tooth as shown in FIG. 8E, or may be one or more other suitable geometrical parameters which can be compared to a corresponding parameter of a set of orthodontic bands to select a proper fitting band for application to the tooth.

Preferably, the geometrical parameter determined for the tooth is a perimeter length of the cross-sections at the steps along the long axis 98. The maximum perimeter length based on the tooth data can be found and compared to corresponding geometrical parameters of the bands. For example, the maximum perimeter length of cross-sections of the tooth can be compared to minimum perimeter lengths along the inner surface of a set of bands. Further, for example, when such a comparison is made, a band whose minimum perimeter length is equal to, or slightly greater than, the maximum perimeter length for the tooth based on the tooth data can be selected for output.

Although any suitable geometrical parameter of the tooth may be used, the geometrical parameter is determined with the tooth 134 in a substantially similar orientation as the orthodontic band, i.e., with the axis of an orthodontic band and axis 98 of tooth 134 aligned. In such a manner, the geometrical parameter of the tooth, e.g., such as perimeter length of a cross-section of the tooth, will correspond to a geometrical parameter of the band, e.g., the inner surface perimeter length along a center line, such as line 65 of orthodontic band 60 in FIG. 5.

The geometrical parameter determination process 82 which includes Blocks 90, 92, and 94 shall be described in further detail. The long axis 98 of a cylinder which best fits the tooth data (Block 90) is determined according to the following process. The best fit cylinder can be defined by computing the minimum distance from a cylinder to every data point on the tooth.

Figure 8D:
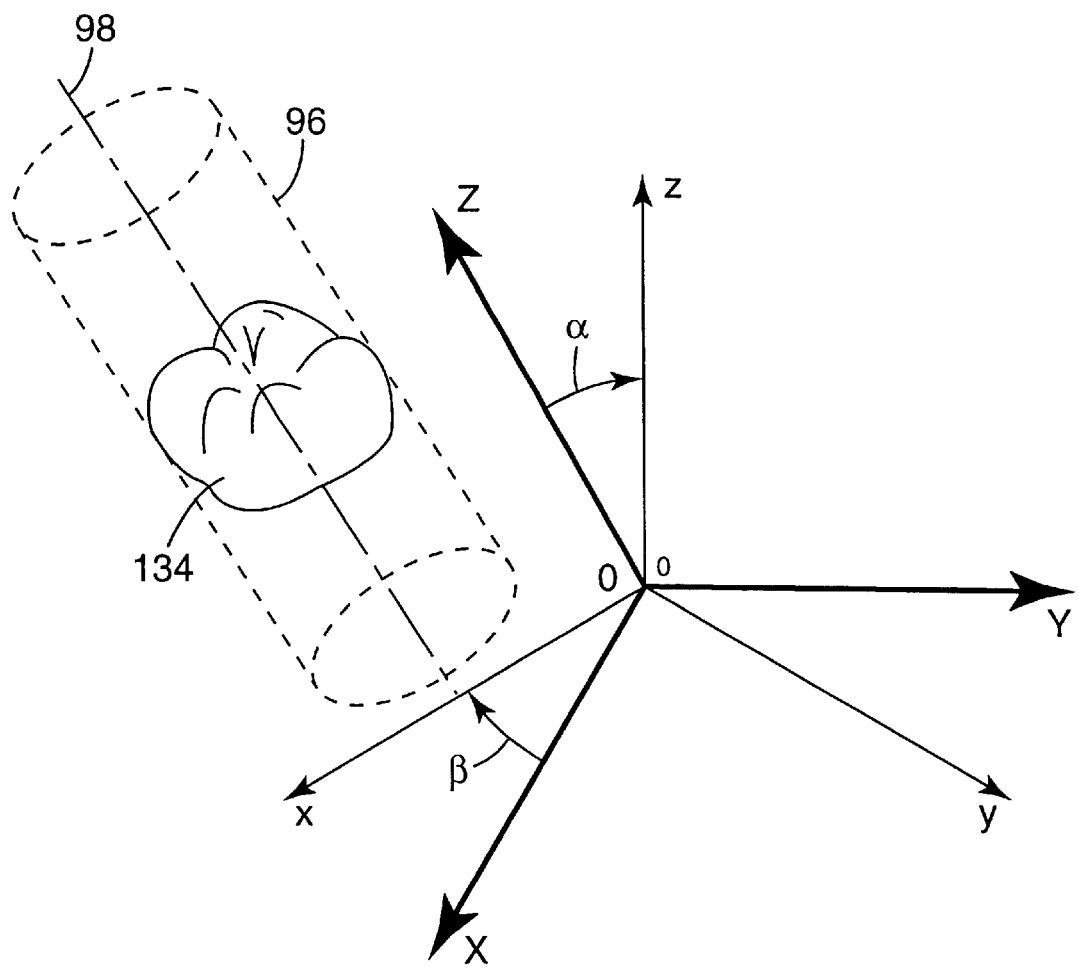
FIG. 8D is the tooth of FIG. 8C shown in a coordinate system used in the method for orthodontic appliance selection of FIG. 8A.

The data representative of the tooth (Block 84) is generally provided in a coordinate system (x,y,z) as shown in FIG. 8D. To attain the best fit cylinder for the tooth data, the tooth data is transformed to a new coordinate system (X,Y,Z). The Z axis of the new coordinate system is parallel to the center, i.e., long, axis 98 of the tooth 134. The transformation to the new coordinate system is performed according to the following equations:

$$\begin{bmatrix} X \\ Y \\ Z \end{bmatrix} = [R_Z]_\beta [R_X]_\alpha \begin{bmatrix} x \\ y \\ z \end{bmatrix}$$

where:

$$[R_Z]_\beta = \begin{bmatrix} \cos\beta & -\sin\beta & 0 \\ \sin\beta & \cos\beta & 0 \\ 0 & 0 & 1 \end{bmatrix}, \text{ and}$$

$$[R_X]_\alpha = \begin{bmatrix} 1 & 0 & 0 \\ 0 & \cos\alpha & -\sin\alpha \\ 0 & \sin\alpha & \cos\alpha \end{bmatrix}.$$

For every data point on the tooth, $X_i = F_z(\alpha, \beta, x_i, y_i, z_i)$ and
$Y_i = F_y(\alpha, \beta, x_i, y_i, z_i)$.

The equation for a cylinder in the (X,Z,Y) coordinate system is:

$$(X-X_c)^2 + (Y-Y_c)^2 = R^2 \text{ where } Z_c = 0$$

and the distance ($\epsilon_i$,) from a point on the tooth to the cylinder surface is:

$$\epsilon_i^2 = R^2 - (X_i - X_c)^2 - (Y_i - Y_c)^2$$

where R is the average size of the tooth data bounding box and $(X_c, Y_c)$ is the center axis of the cylinder.

Solving the least square equations results in $(X_c, Y_c)$ and $(\alpha, \beta,)$:

$$\frac{\partial \sum_0^n \varepsilon_i}{\partial X_C} = 0$$

$$\frac{\partial \sum_0^n \varepsilon_i}{\partial Y_C} = 0 \Rightarrow (X_C, Y_C) \text{ and } (\alpha, \beta)$$

$$\frac{\partial \sum_0^n \varepsilon_i}{\partial \alpha} = 0$$

$$\frac{\partial \sum_0^n \varepsilon_i}{\partial \beta} = 0$$

As such the center axis of the cylinder and thus the center axis 98, i.e., long axis, of the tooth is $(X_c, Y_c)$ and all calculations to follow can be made relative to the long axis in the new coordinate system.

With the long axis 98 of the tooth 134 determined (Block 90), the stepwise perimeter length of a cross-section perpendicular to the long axis 98, is performed (Block 92). The values for the geometrical parameter are searchable along the long axis 9 and a maximum value of the geometrical parameter can be determined (Block 94). For example, the searching process may involve moving along the axis 98 in relatively large steps to locate a transition from a maximum geometrical parameter for a cross-section to a smaller geometrical parameter for a cross-section, and then performing such computations again in smaller steps in the transition region. The searching process may go through several iterations to arrive at a maximum geometrical perimeter. When the maximum geometrical parameter for the tooth data along the long axis 98 is found, it is then used for comparison (Block 88) to corresponding geometrical parameters of the bands (Block 86).

For example, if the geometrical parameter to be determined for the tooth data is perimeter length, the following is performed. First, as described above, the long axis of the cylinder 96 which best fits the tooth data is determined (Block 90). Then, the perimeter lengths for cross-sections lying orthogonal to the long axis 98 are determined (Block 92). The perimeter length may be computed in various manners, as would be known to one skilled in the art. For example, as shown in FIG. 8E, the perimeter length is computed using a measurement tool for drawing line segments 104 about the perimeter of the cross-section. The lengths of the line segments 104 are then summed to obtain a perimeter length, e.g., 3.1 cm. The maximum value of the perimeter length of the various cross sections taken along the long axis 98 is then found, e.g., such as by numerous iterations and calculations as described above.

With the maximum perimeter length calculated, the maximum perimeter length can be compared to minimum perimeter lengths of the inner surfaces of a set of orthodontic bands (Block 88). The band whose minimum perimeter length is equal to, or slightly greater than, the maximum perimeter length of the tooth, is then selected for application to tooth 134 (Block 89 and Block 87). For example, the perimeter length of the inner surface used for comparison to the maximum perimeter length of the tooth may be the perimeter length of any circumferential line lying in a plane orthogonal to the axis of the band, but is preferably the center line, i.e., the midpoint between the ends of the band, as previously described. The output of the appropriate band to be applied to the tooth is provided (Block 89) based on the comparison (Block 88), e.g., by display, text, or any other method of providing information to the user by the system.

One skilled in the art will recognize that the corresponding band parameters compared to the determined tooth geometrical parameters will be dependent on what geometrical parameter of the tooth is determined. For example, if a maximum cross-section area of the tooth is determined then the corresponding band parameters compared will likely be minimum cross-section areas for the band, e.g., an area defined by the minimum perimeter of a band at the inner surface thereof. Further, if a maximum width of the tooth is determined, then the corresponding band parameters may be widths of the bands.

Another illustrative embodiment of an orthodontic band selection method 121 is shown and described with reference to FIGS. 9A–9E. The orthodontic band selection method 121 includes determining a geometrical parameter of a tooth (Block 122), e.g., tooth 134 of FIG. 8B, from digital data representative of tooth 134 (Block 170). The geometrical parameter determination process (Block 122) of the orthodontic band selection method 121 includes determining a best-fit occlusal plane for the tooth 134 (Block 123). Using the best-fit occlusal plane, a tooth center point 137 and center axis 136 extending through tooth 134 (as shown in FIGS. 9C and 9E) is determined (Block 124). A maximum cross-section area in a plane lying orthogonal to the axis 136, as shown by line 138 of FIG. 9C and the cross-section drawing of FIG. 9E, is then used to determine a particular tooth geometrical parameter for use in comparison to corresponding band geometrical parameters (Block 172).

It will be recognized that the main difference between the embodiment described with reference to FIGS. 8A–8E and this embodiment described with reference to FIGS. 9A–9E is the manner in which the long axis of the tooth is determined. For example in the embodiment described with reference to FIGS. 8A–8E, the long axis 98 of the tooth is determined using a best fit cylinder process. In contrast, the embodiment described with reference to FIGS. 9A–9E determines the long axis 136 of the tooth with use of a best fit occlusal plane.

One skilled in the art will recognize that the geometrical parameter generated by geometrical parameter determination process 122 using the digital data representative of tooth 134 (Block 170), and the geometrical parameter determination process itself, may take one of many forms as described previously with respect to FIGS. 8A–8E. For example, the geometrical parameter determined may be a perimeter length of the cross-section of the tooth 134 orthogonal to axis 136 as shown in FIGS. 9C and 9E, the geometrical parameter may be the cross-section area as represented by the lined area shown in FIG. 9E, the geometrical parameter may be an integrated volume of a slice of tooth 134 (as represented generally by dashed lines 153 of FIG. 9C), or the geometrical parameter may be one or more other suitable geometrical parameters which can be compared to a corresponding parameter of a set of orthodontic bands to select a proper band, e.g., a maximum width of a cross-section, etc.

Preferably, the geometrical parameter determined is a perimeter length of the maximum cross-section area lying in a plane (represented by line 138) orthogonal to axis 136 (FIG. 9C). The plane 138 is preferably parallel to the best fit occlusal plane 155. The best fit occlusal plane 155 is defined as a plane including three or more maximum points of the tooth with the remaining portions of the tooth lying on one side of the plane or the other, and further wherein the best fit plane is perpendicular to the center, i.e., long, axis 136 of the tooth. For example, as shown in the side view of FIG. 9C and the top view of FIG. 9D, plane 155 includes or contacts the tooth at three points 157.

Just as described with reference to the embodiment of FIGS. 8A–8E, although any suitable geometrical parameter of the tooth may be used, the geometrical parameter is determined with the tooth 134 in a substantially similar orientation as the orthodontic band, i.e., with the axis 63 of an orthodontic band and axis 136 of tooth 134 aligned. In such a manner, the geometrical parameter of the tooth, e.g., such as perimeter length at cross-section area 138, will correspond to a geometrical parameter of the band, e.g., the inner surface perimeter length along a center line, such as line 65 of orthodontic band 60 in FIG. 5.

After the geometrical parameter of the tooth is determined by geometrical parameter determination process 122, the determined geometrical parameter is compared (Block 173) to data representative of corresponding geometrical parameters of a set of orthodontic bands (Block 172). A resultant output orthodontic band is selected (Block 175) based on the comparison (Block 173).

Figure 9A:
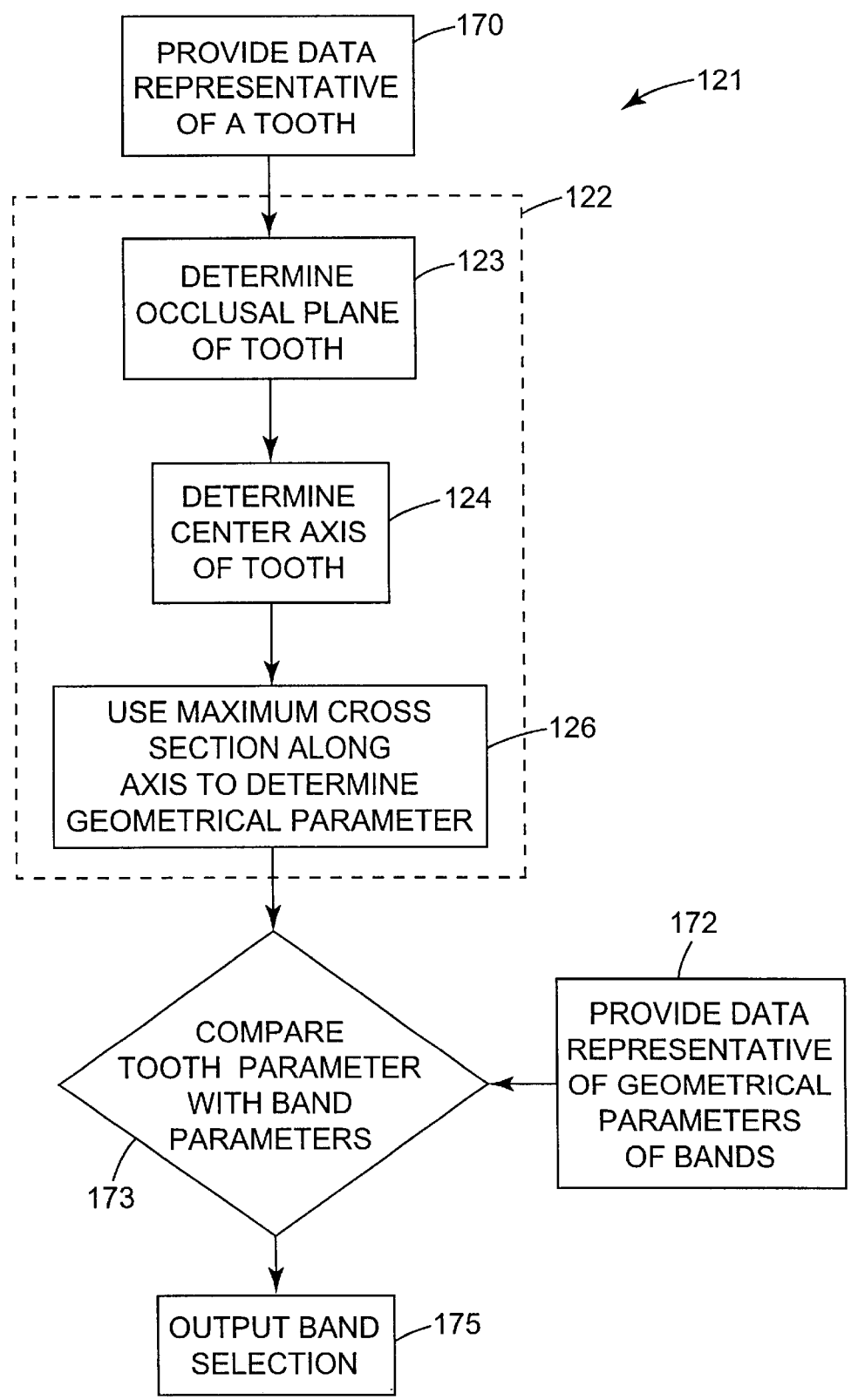
FIG. 9A is a flow diagram illustrating another embodiment of a method for orthodontic appliance selection according to the present invention.
Figure 9B:
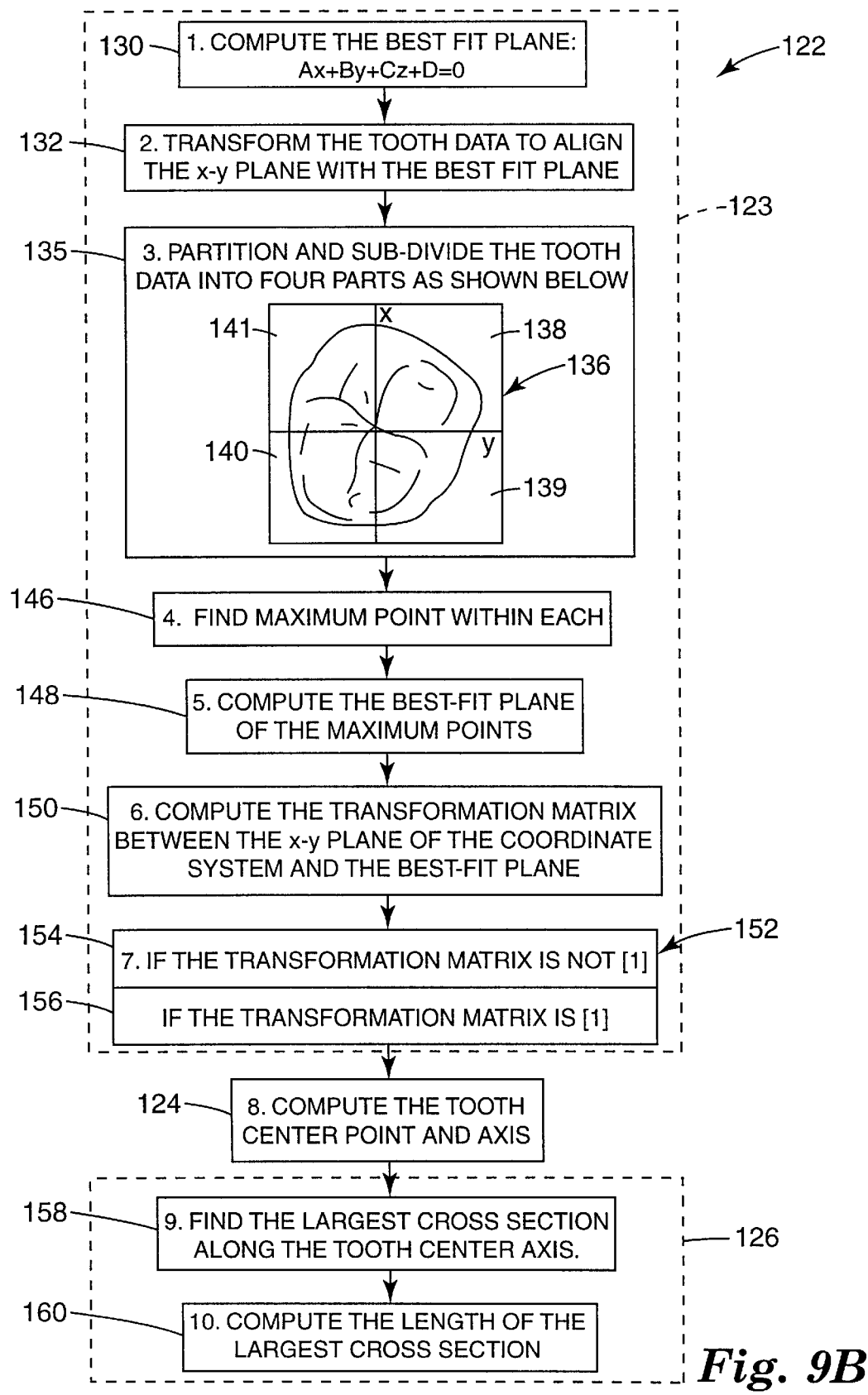
FIG. 9B is a more detailed flow diagram of the geometrical parameter determination process shown in FIG. 9A.
Figure 9C:
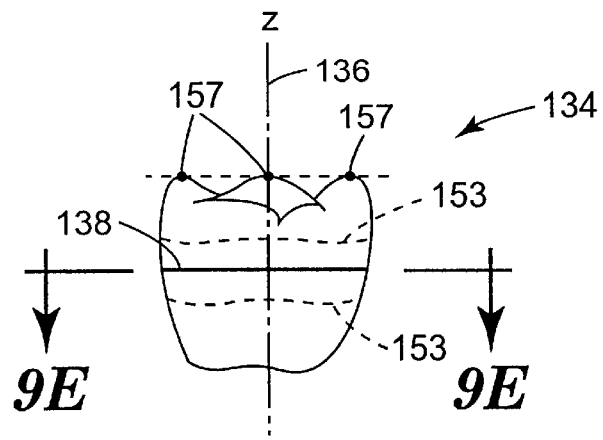
FIG. 9C is a side view of the tooth of the lower arch shown in FIG. 8B for which a band is to be selected according to the process shown in FIGS. 9A and 9B.
Figure 9D:
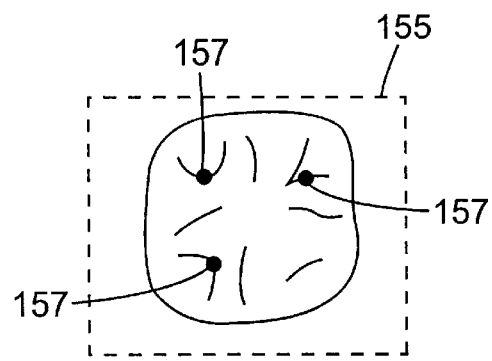
FIG. 9D is a top view of the tooth of FIG. 9C.
Figure 9E:
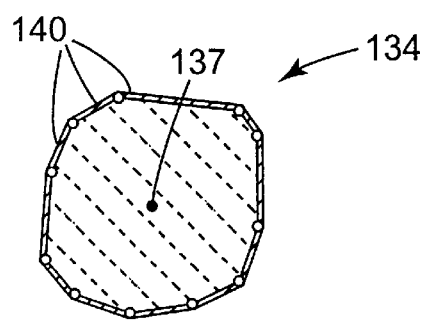
FIG. 9E is a cross-section view of the tooth of FIG. 9C taken at line 9E—9E thereof.

One illustrative embodiment of geometrical parameter determination process 122 which includes Blocks 123, 124, and 126 is shown in further detail in FIG. 9B. The perimeter length of a maximum cross-section area lying in a plane orthogonal to the center axis 136 of tooth 134 (shown in FIG. 9C–9E) with the orthogonal plane being parallel to the occlusal plane of the tooth and at a certain depth within the tooth is determined in the following manner. First, a best-fit occlusal plane of the tooth is determined (Block 123). As indicated above, the occlusal plane is defined as a plane including three or more maximum points of the tooth with the remaining portions of the tooth lying on one side of the plane, e.g., the maximum points are the points which will be in contact with other teeth when the upper and lower dental arches are in occlusion (e.g., intercuspation).

To find the best-fit occlusal plane, an initial occlusal plane F (x,y,z) is computed (Block 130); wherein F (x,y,z)=Ax+By+Cz+D=0. With each point P (x,y,z) of the tooth known and the plane F (x,y,z)=Ax+By+Cz+D=0, the distance (d) from each point of the tooth to the plane can be expressed as d=D (P,F) or more particularly:

$$d = \frac{Ax_1 + By_1 + Cz_1 + D}{\pm\sqrt{A^2 + B^2 + C^2}}$$

The distance from all the points P to plane ($\epsilon$) can then be expressed as follows:

$$\epsilon = \Sigma d^2$$

To compute the initial occlusal plane, the following equations can be used to solve for A, B, C, and D and thus obtain the initial plane:

$$\frac{\partial \epsilon}{\partial A} = \sum \frac{\partial d^2}{\partial A} = 0$$

$$\frac{\partial \epsilon}{\partial B} = \sum \frac{\partial d^2}{\partial B} = 0$$

$$\frac{\partial \epsilon}{\partial C} = \sum \frac{\partial d^2}{\partial C} = 0$$

$$\frac{\partial \epsilon}{\partial D} = \sum \frac{\partial d^2}{\partial D} = 0$$

The data representative of tooth 134 is then transformed to align the x-y lane of the coordinate system being used with the initial occlusal plane (Block 132). Such alignment assists in the determination of maximum points of the tooth for use as described below. In other words, the tooth is being transformed to align with the coordinate system such that the long axis of the tooth corresponds to the z-axis of the coordinate system.

The transformed tooth data is then partitioned and subdivided into four portions, as illustrated by image 136 of Block 135. The image 136 of tooth 134 thus includes portions 138–141. Thereafter, a maximum point is located within each portion, 138–141 (Block 146) and an updated occlusal plane of the maximum points within each of the partitions (Block 148) is computed in the same manner as described above for the initial occlusal plane only using the maximum points within the partitions.

A transformation matrix between the x-y plane of the coordinate system and the updated occlusal plane, as computed using the maximum points in the partitions, is then computed (Block 150). As shown in Block 152, if the transformation matrix is not [1] (Subblock 154), then the process of steps 132, 135, 146, 148, and 150 are repeated until a transformation matrix of [1] is attained. As shown in Subblock 156, if the transformation matrix of [1] is attained, the updated occlusal plane during that cycle is considered the best-fit occlusal plane from which further calculations can be made.

One skilled in the art will recognize that the best fit occlusal plane may also be determined by positioning a surface plane on the tooth. With the surface plane positioned on the tooth, the points of contact between the tooth and the surface plane can be determined. Such contact points are much like the maximum points of the tooth determined by the partitioning method as described with reference to FIG. 9B. The contact points can then be used to define the best-fit occlusal plane and used to find the center point and axis as described further below.

Further, the best fit occlusal plane can be provided in a number of other manners. For example, a best fit occlusal plane can be estimated by an operator who picks three points that define it. In addition, the best fit occlusal plane can be determined automatically using the best fit cylinder described above with reference to FIGS. 8A–8E. For example, the face of the best fit cylinder can be used as the best fit occlusal plane.

Using the best-fit occlusal plane determined by Block 123, the tooth center point is computed (Block 124) by summing the points (P) on the best-fit occlusal plane and then dividing by the number of points (N) to find the center point in accordance with the following equation:

$$P_{center} = \frac{\sum_N P_i}{N}$$

From the tooth center point $P_{center}$ (x,y,z), the tooth center axis is: $x = X_{center}$ and $y = Y^{center}$, where z=0.

With the tooth center axis, i.e., long axis, of the tooth 136 determined (Block 124), the maximum cross-section along the center axis 136 is searchable and can be determined (Block 158). The searching process may involve moving along the axis in relatively large steps to located a transition from a maximum cross-section to a smaller cross-section, and then performing such computations again in smaller steps in the transition region. The searching process may go through several iterations to arrive at a maximum cross-section area. When the maximum cross-section lying orthogonal to axis 136 is found, the perimeter length of the cross-section lying in the orthogonal plane is computed (Block 160).

The perimeter length may be computed in various manners, as would be known to one skilled in the art. For example, as shown in FIG. 9E, the perimeter length is computed using a measurement tool for drawing line segments 140 about the perimeter of the cross-section. The lengths of the line segments are then summed to obtain a perimeter length.

With the maximum perimeter length calculated, the perimeter length can be compared to the corresponding perimeter length of the inner surfaces of a set of orthodontic bands, one of which is to be selected for application to tooth 134 (Block 173, 175). An output of the appropriate band is provided (Block 175) based on the comparison, e.g., by display text, etc.

It will be readily apparent to one skilled in the art that the routines as described with reference to the figures herein may or may not require user input. For example, the geometrical parameter determination routines may be initiated by a user selecting a display icon after a particular tooth is selected, resulting in an output of a particular orthodontic band. However, it should also be apparent to one skilled in the art that steps along the process may be supplied with user input, such as the use of measurement tools in measuring the perimeter length, etc.

All references and patents disclosed herein are incorporated by reference in their entirety as if each were individually incorporated. Various modifications and alterations of this invention will become apparent to those skilled in the art without departing from the scope of the invention, and it should be understood that this invention is not to be unduly limited to the illustrative embodiments and processes set forth herein.

What is claimed is:

1. An article comprising a container and a set of orthodontic bands received in the container, wherein each of the set of orthodontic bands has substantially a same fundamental geometrical configuration, wherein each of the orthodontic bands is of a different size relative to the other orthodontic bands, and further wherein each orthodontic band has a precoat adhesive material applied to at least a portion thereof.

2. The article of claim 1, wherein the precoat adhesive material is uniformly spread on an inner surface of each orthodontic band.

3. An article comprising a container and a set of orthodontic bands received in the container, wherein each of the set of orthodontic bands has substantially a same fundamental geometrical configuration, wherein each of the orthodontic bands is of a different size relative to the other orthodontic bands, and further wherein each orthodontic band has a precoat adhesive material applied to at least a portion thereof, and further wherein the precoat adhesive material is distributed on at least a portion of at least one orthodontic band based on a calculated volume difference between an inner surface of the at least one orthodontic band and the tooth of the patient.

* * * * *

UNITED STATES PATENT AND TRADEMARK OFFICE
CERTIFICATE OF CORRECTION

PATENT NO. : 6,350,119 B1
DATED : February 26, 2002
INVENTOR(S) : Jordan, Russell A.

It is certified that error appears in the above-identified patent and that said Letters Patent is hereby corrected as shown below:

Column 10,
Line 46, following "stepwise" and before "perimeter" insert -- process of determining values for a geometrical parameter of the tooth, e.g., a --.
Line 49, delete "9" and insert in place thereof -- 98 --.

Column 14,
Line 15, delete "$Y^{center}$" and insert in place thereof -- $Y_{center}$ --.

Signed and Sealed this

Fifth Day of November, 2002

Attest:

Attesting Officer

JAMES E. ROGAN
*Director of the United States Patent and Trademark Office*